United States Patent [19]

Kubla et al.

[11] Patent Number: 4,666,913
[45] Date of Patent: May 19, 1987

[54] HYDROXY AND AMINOTHIAZOLYL-BENZODIAZINONE COMPOUNDS, CARDIOTONIC COMPOSITIONS INCLUDING THE SAME, AND THEIR USES

[75] Inventors: Donald E. Kubla, Doylestown; Henry F. Campbell, Lansdale; William L. Studt, Harleysville; Bruce F. Molino, Lansdale; Thomas J. Tucker, North Wales, all of Pa.

[73] Assignee: William H. Rorer, Inc., Fort Washington, Pa.

[21] Appl. No.: 801,071

[22] Filed: Nov. 22, 1985

[51] Int. Cl.$^4$ ................. A61K 31/505; C07D 417/02
[52] U.S. Cl. .................... 514/259; 514/220; 514/221; 514/249; 514/250; 514/269; 514/267; 514/270; 514/366; 540/500; 540/504; 540/517; 540/493; 540/495; 544/284; 544/231; 544/354; 548/147; 548/181
[58] Field of Search ............ 544/284, 354, 231; 548/181, 147; 260/245.5; 514/259, 221, 249, 269, 270, 220, 250, 267, 366; 540/514, 517, 500

[56] References Cited

U.S. PATENT DOCUMENTS

| | | | |
|---|---|---|---|
| 4,004,012 | 1/1977 | Lesher et al. | 546/257 |
| 4,072,746 | 2/1978 | Lesher et al. | 546/257 |
| 4,107,315 | 8/1978 | Lesher et al. | 546/257 |
| 4,137,233 | 1/1979 | Lesher et al. | 546/257 |
| 4,199,586 | 4/1980 | Lesher et al. | 546/257 |
| 4,251,531 | 2/1981 | Doria et al. | 544/284 |
| 4,271,168 | 6/1981 | Lesher et al. | 546/257 |
| 4,338,329 | 7/1982 | Paget et al. | 548/181 |
| 4,361,568 | 11/1982 | Lesher et al. | 546/119 |
| 4,374,141 | 2/1983 | Lesher et al. | 546/257 |
| 4,375,467 | 3/1983 | Lesher et al. | 546/119 |
| 4,387,223 | 6/1983 | Yamamoto et al. | 544/284 |
| 4,414,390 | 11/1983 | Tominaga et al. | 546/121 |
| 4,415,572 | 11/1983 | Tominaga et al. | 544/363 |
| 4,418,070 | 11/1983 | Okonogi et al. | 548/182 |
| 4,432,979 | 2/1984 | Campbell | 544/333 |
| 4,514,400 | 4/1985 | Campbell | 514/252 |
| 4,521,416 | 6/1985 | Sircar et al. | 514/252 |
| 4,526,895 | 7/1985 | Jarreau et al. | 514/341 |
| 4,526,982 | 7/1985 | Morrison | 548/336 |
| 4,539,321 | 9/1985 | Campbell | 514/252 |

FOREIGN PATENT DOCUMENTS

| | | |
|---|---|---|
| 0126651 | 11/1984 | European Pat. Off. |
| 0132817 | 2/1985 | European Pat. Off. |
| 0148623 | 7/1985 | European Pat. Off. |
| 57-01706 | 5/1982 | Japan . |
| WO81/02575 | 9/1985 | PCT Int'l Appl. |
| 2070606 | 9/1981 | United Kingdom . |

OTHER PUBLICATIONS

Bachman and Heisey, "The Preparation of Vinyl Derivatives of Five-Atom Heterocyclic Rings," J. Am. Chem. Soc. 21, pp. 1985-1988 (1949).
Archer and Sternbach, "The Chemistry of Benzodiazepines," Chem. Rev. 68, pp. 747-784 (1968).
Coyne and Cusic, "3,4-Dihydro-2(1H)-Quinazolinones," J. Med. Chem. 11, pp. 1208-1213 (1968).
Gschwend & Fuhrer, "Ortho Functionalization of Aromatic Amines; Ortho Lithiation," J. Org. Chem. 44, pp. 1133-1136 (1979).
Boots, et al., "Conformational Aspects of Ureas in the Inhibition of the Hill Reaction," J. Med. Chem. 13, p. 144 (1969).
Bristol, et al., "Cardiotonic Agents," J. Med. Chem. 27, pp. 1099-1101 (1984).
Chemical Abstracts 73: 77279n (1970); Bernardi, et al., Anticonvulsive Quinazolinones, Ger. Offen. 1,958,515 (1970).
Chemical Abstracts 82: 43315s (1975); Pilicheva, et al., New Rearrangement in the Quinazoline Series, Dokl. Akad. Nauk SSSR, 1974, 218(b), 1375-76.

*Primary Examiner*—Glennon H. Hollrah
*Assistant Examiner*—James H. Turnipseed
*Attorney, Agent, or Firm*—James A. Nicholson; Alexis Barron; Martin F. Savitzky

[57] ABSTRACT

A method for increasing cardiotonic contractility in humans or other animals using a class of hydroxy and aminothiazolyl-benzodiazinone compounds and pharmaceutical compositions including the same.

21 Claims, No Drawings

HYDROXY AND AMINOTHIAZOLYL-BENZODIAZINONE COMPOUNDS, CARDIOTONIC COMPOSITIONS INCLUDING THE SAME, AND THEIR USES

FIELD OF THE INVENTION

This invention relates to substituted benzodiazinones useful as cardiotonic agents for the treatment of congestive heart failure. This invention also relates to methods for increasing cardiac contractility using said compounds, and pharmaceutical compositions including said compounds.

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Inotropic drugs include the 5-pyridyl substituted pyridones disclosed in U.S. Pat. Nos.: 4,004,012; 4,072,746; 4,107,315; 4,137,233; 4,199,586; 4,271,168; and 4,107,315; in GB 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572 and the 5-phenyl-thiazole compounds disclosed in U.S. Pat. No. 4,418,070.

Cardiotonic bicyclic heteroaryl-5-substituted pyridyl compounds are disclosed in U.S. Ser. No. 410,646, filed Aug. 23, 1982, now abandoned, and cardiotonic diazaheterocyclic-5-substituted pyridyl compounds are disclosed in U.S. Pat. No.4,432,979 and U.S. Pat. Nos. 4,514,400 and 4,539,321 all of which are assigned to the same assignee as the present application.

Cardiotonic 4,5-dihydro-5-[4-(H-imidazol-1-yl)phenyl]-3(2H)-pyridazinones are disclosed in Bristol et al., *J. Med. Chem.* 22, 1099 (1984); cardiotonic imidazolyl substituted pyridazinones are disclosed in U.S. Pat. No. 4,521,416, and cardiotonic benzothiazolone substituted pyridazinones are disclosed in published EPO Patent Application Ser. No. 84108656.4 (Publ. No. 0132817). Cardiotonic compounds including a pyrazole group are disclosed in published EPO Patent Application Ser. No. 84303456.2 (Publ. No. 0126651) and U.S. Pat. Nos. 4,526,895 and 4,526,982.

SUMMARY OF THE INVENTION

The present invention relates to a class of heterocyclic substituted benzodiazinone compounds which exhibit cardiotonic activity in humans and mammals.

The preferred compounds of the present invention include benzodiazinones substituted by either an amino- or hydroxy-substituted thiazole ring.

This invention relates particularly to the benzodiazinone compounds within the scope by Formula I:

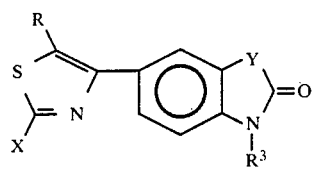

wherein:
X is $NR^1R^2$ or OH;
Y is

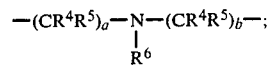

a and b are 0, 1 or 2, provided that a+b is not greater than 2;
R, $R^1$, $R^2$, $R^3$, $R^4$, $R^5$ and $R^6$ are each independently H, alkyl or aralkyl;
$R^4$ groups on vicinal carbon atoms may together form a carbon-carbon double bond; and
geminal $R^4$ and $R^5$ groups may together form a spiro substituent, $-(CH_2)_d-$, where d is 2 to 5;
or a pharmaceutically acceptable salt thereof.

This invention also relates to the use of such compounds in pharmaceutical compositions which are effective in increasing cardiac contractility in humans and to the uses of such compositions for the treatment of cardiac failure in humans and other mammals.

DETAILED DESCRIPTION

Certain of the compounds encompassed within the present invention, and particularly, compounds of Formula I, may exist in enolic or tautomeric forms, and all of these forms are considered to be included within the scope of this invention.

The compounds of this invention which have particular usefulness as cardiotonic agents are described by Formula I wherein the benzodiazinone ring is described by one of Formulae II, IIIa, IIIb or IVa-IVc:

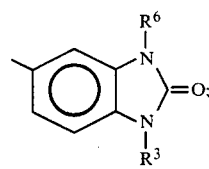

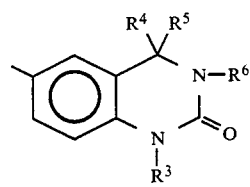

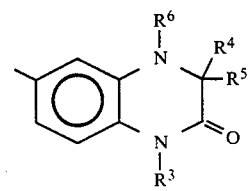

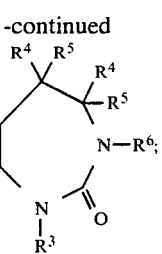

IVa

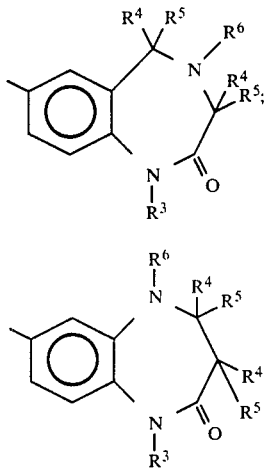

IVb

IVc wherein:

R³, R⁴, R⁵ and R⁶ are as described above.

A most preferred class of compounds within the present invention includes compounds of Formulae I, II, IIIa and IVa wherein at least one of R, R¹, R², R³, R⁴, R⁵ or R⁶ is other than hydrogen.

More preferred compounds are those disclosed by Formula I, wherein:
either R³ or R⁴ or R⁶ is lower alkyl.

A special embodiment of the present invention comprises compounds of Formula I where R⁴ and R⁵ form a spiro ring system, an example of which is shown by Formula V:

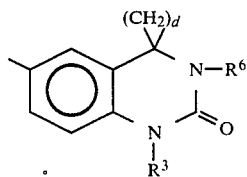

V

As employed above and throughout the disclosure, the following terms, unless otherwise indicated, shall be understood to have the following meanings:

"Alkyl" means a saturated aliphatic hydrocarbon which may be either straight- or branched-chained containing from about one to about 6 carbon atoms.

"Lower alkyl" means an alkyl group as above, having 1 to about 4 carbon atoms.

"Aryl" means an aromatic hydrocarbon radical. The preferred aryl groups are phenyl and substituted phenyl.

"Aralkyl" means an alkyl group substituted by an aryl radical. The preferred aralkyl groups are lower alkyl groups substituted by phenyl or substituted phenyl.

"Substituted phenyl" means a phenyl groups substituted by one or more of lower alkyl, lower alkoxy, amino, lower alkyl amino, lower alkyl mercapto, hydroxy lower alkyl, acetoxy, benzyloxy, phenoxy, lower alkyl sulfinyl or lower alkyl sulfonyl.

"Hydroxy alkyl" means an alkyl group substituted by a hydroxy group. Hydroxy lower alkyl groups are preferred and include hydroxymethyl, 2-hydroxyethyl, 2-hydroxypropyl, and 3-hydroxypropyl.

"Alkoxy" means an alkyl oxy radical group. Lower alkoxy groups are preferred and include methoxy, ethoxy, n-propoxy, i-propoxy, sec-propoxy, n-butoxyl among others.

"Alkyl mercapto" means a radical of the formula —S—R where R is alkyl. Lower alkyl mercapto groups are preferred.

"Alkylsulfinyl" means a R—SO— radical where R is alkyl.

"Alkylsulfonyl" means a R—SO₂— radical where R is alkyl. Lower alkyl sulfonyl groups are preferred.

"Amino" means —NH₂ and "alkyl amino" means —NHR where R is alkyl. Lower alkyl amino groups are preferred.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds within the scope of Formula I may be prepared in accordance with the following reaction sequences.

Treatment of a benzodiazinone intermediate VI (when a≠0) with an acyl halide under Friedel-Crafts reaction conditions forms the acylation adduct VII. Ring closure to afford the aminothiazole compounds of Formula I is accomplished with an appropriately substituted thiourea. Reactions of the adduct VII with potassium thiocyanide followed by treatment with acetic acid/sulfonic acid) mixture yields the hydroxythiazole compounds. See Scheme I below.

Scheme I

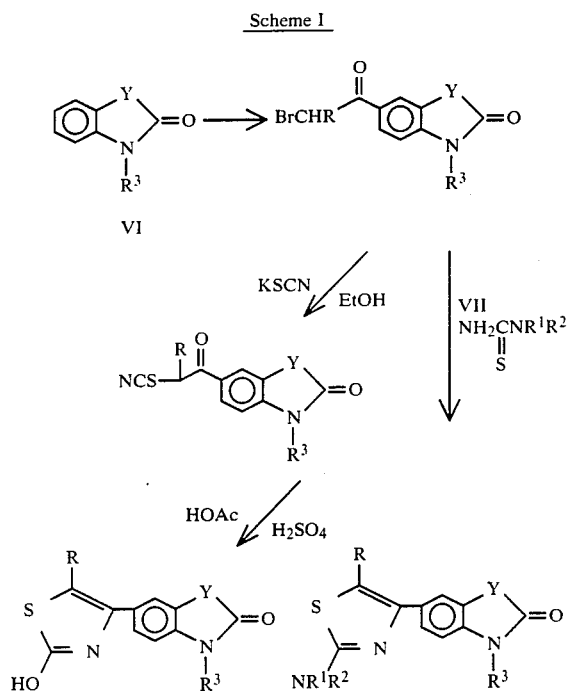

The benzodiazinone intermediates VI, particularly the unsubstituted and lower alkyl substituted compounds are either known compounds or may be prepared in accordance with the reaction sequences described below.

The 3,4-dihydro-2(1H)-quinazolinone intermediates may be prepared from analogous 2-carbamoyl anilines by reducing the carbamoyl functionality to the methylene amine. Treatment of the resulting diamine with carbonyldiimidazole in THF affords the 3,4-dihydro-2(1H)-quinazolinone. See Scheme II below.

Scheme II

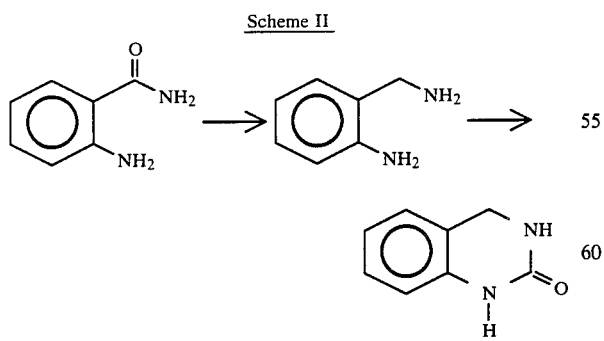

When b=0, a=1 and at least one of $R^4$ or $R^5$ is hydrogen in Formula I above and $R^3$ is as described above, the intermediate quinazolinone may be prepared as shown in Scheme III below.

Scheme III

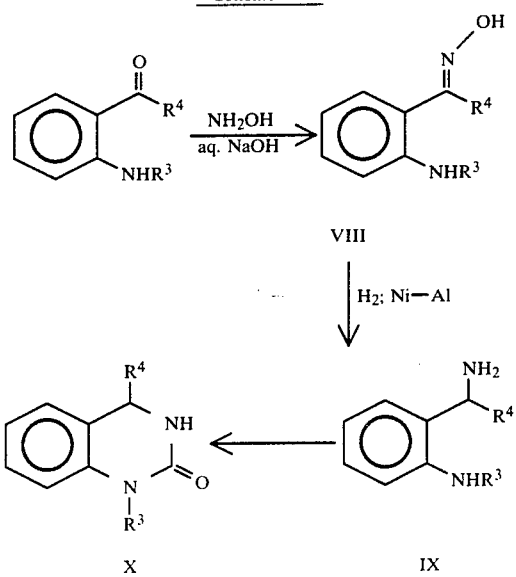

Treatment of 1-$R^4$-(2-$R^3$-substituted aniline)ketone with hydroxylamine and aqueous sodium hydroxide affords the oxime, VIII. Reduction, preferably using Al-Ni catalyst, results in the amine IX, which may be cyclized, using carbonyldiimidazole, to the $R^4$-substituted-2(1H)-quinazolinone. When $R^3$ is hydrogen in Scheme III above, the $R^4$ substituted intermediate, X, may be alkylated selectively in the $R^3$ position using a hydride reagent in a polar aprotic solvent and an appropriate alkylating reagent, preferably sodium hydride in DMSO.

The preparation of $R^6$-substituted benzodiazinone intermediates is shown in Scheme IV below.

Scheme IV

Catalytic hydrogenation of a $R^6$-substituted-2-nitrobenzamide followed by the hydride reduction of the $R^6$-substituted-2-amino-benzamide results in the methylene diamine which may be cyclized to the $R^6$-substituted -2(1H)-quinazolinone. See, M. R. Boots, S. G. Boots, *J. Med. Chem.*, 13, 144 (1969). Alkylation of the 1-N position affording $R^3$-substitution may be accomplished at this stage. See, W. E. Coyne and J. W. Cusic, infra. Another method for the preparation of the $R^6$ substituted quinazolinone intermediates involves the rearrangement of a quinazolidinol as reported in Pilicheva, et al., *Dokl. Akad. Nauk* SSSR 1974, 218(6), 1375–6.

Another method for the preparation of $R^3$-substituted 2H-quinazolinones is described by W. E. Coyne and J. W. Cusic, *J. Med. Chem.*, 11, 1208 (1968), hereby incorporated by reference. Treatment of a 1-N-substituted isatoic anhydride with ammonia affords the 2-substituted amino benzamide, which may be reduced to the diamine and cyclized to the 1-N substituted intermediate as described above. The 3-position may be alkylated to give the 1-$R^3$, 3-$R^6$-disubstituted intermediate compounds.

The spiro compounds of Formula I, wherein $R^4$ and $R^5$ together are $(CH_2)_d$, may be prepared from the 2-nitro styryl intermediate, XI, as shown in Scheme V below.

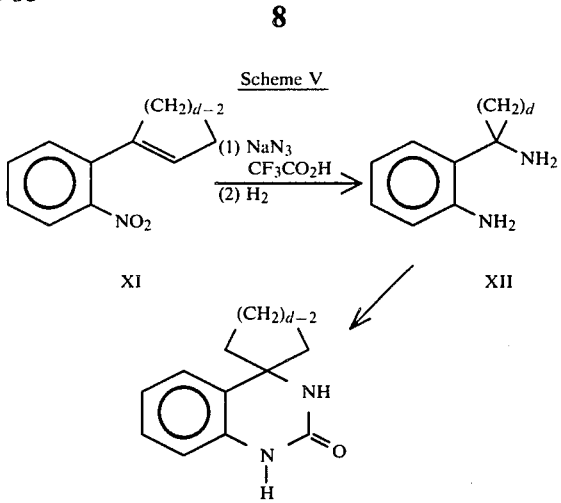

Scheme V

Treatment of the styryl intermediate with sodium azide in trifluoroacetic acid, followed by the reduction of the nitro and azido groups results in the diamine intermediate, XII. Cyclization with carbonyl diimidazole results in the spiro benzodiazinone intermediate.

The spiro compounds may also be derived from the 2-amino styryl intermediate, which may be prepared from aniline according to Scheme VI, below.

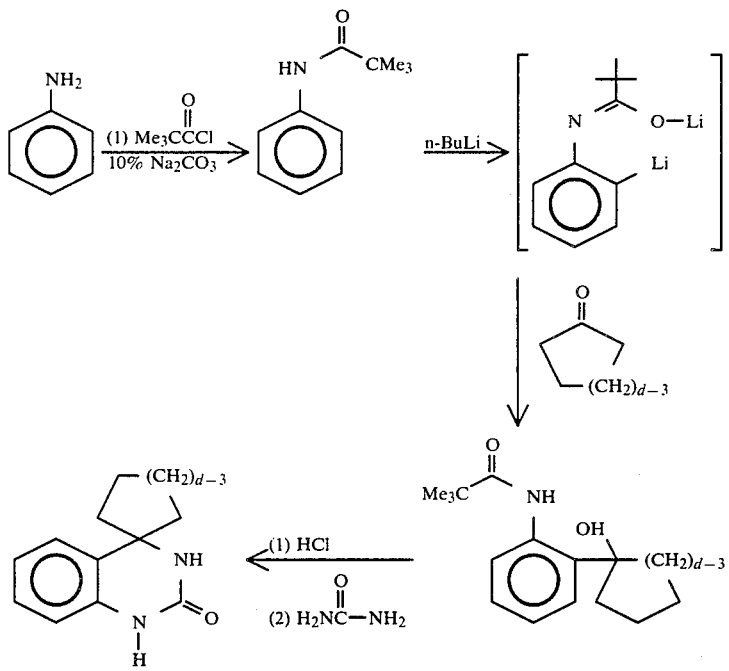

Scheme VI

Treatment of aniline with a trialkylacetyl chloride, such as trimethylacetyl chloride in methylene chloride and 10% aqueous alkali metal carbonate, results in the trialkyl acetamide. Treatment of the amide with n-butyl lithium forms the metallated intermediate, shown above, which is reacted with a carbocyclic ketone, thereby forming the tertiary alcohol intermediate. See, H. Gschwend, W. Fuhrer, *J. Org. Chem.* 44, 1133, 1979. The alcohol may be dehydrated and the amine deprotected in one step by acid hydrolysis using, for example, aqueous hydrochloric acid. Cyclization to the spiro benzodiazinone intermediate may be accomplished by heating a neat mixture of the amine and urea to about 100° to about 200° C. See, L. Bernardi et al., *Ger. Offen.* No. 1,958,515 (1970), hereby incorporated by reference. Alternatively, the mixture may be heated to cyclization temperatures, about 100° to about 200° C., preferably in an aprotic polar solvent, for about 15 min. to about two days.

The 7-membered benzodiazepinone compounds of Formula I may be prepared according to Scheme VII below.

Scheme VIII

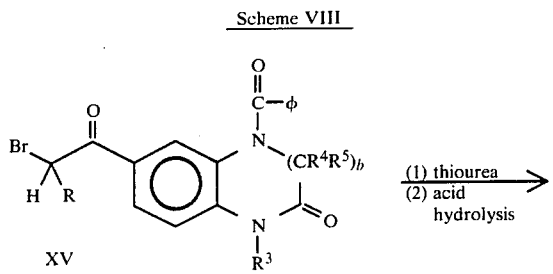

Scheme VII

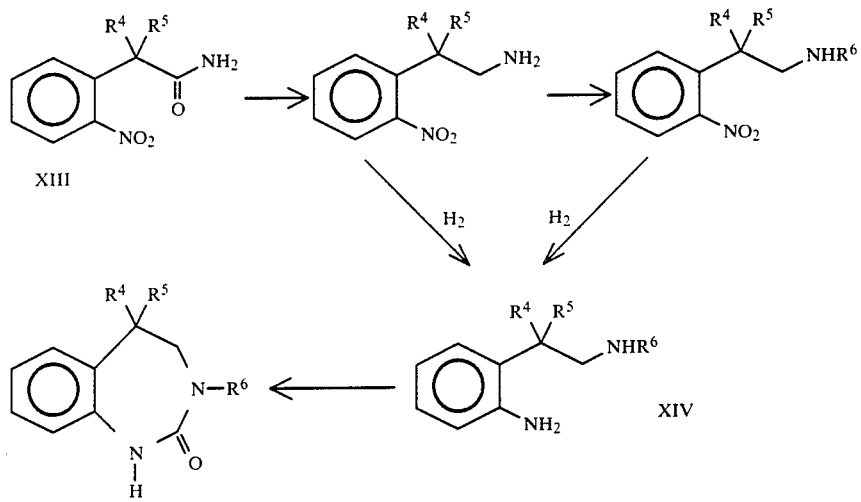

Reduction of the 2-nitrobenzylamide XIII with diborane followed by the catalytic hydrogenation of the nitro group affords the diamine intermediate, XIV. Treatment of the diamine intermediate with carbonyldiimidazole results in the benzodiazepinone intermediate. Either the diamine intermediate, XIV, or the benzodiazepinone intermediate may be alkylated, affording the 1- and/or 3-substituted benzodiazepinone compounds.

When a=0 in Formula I above, the compounds of this invention may be prepared from the α-halo keto-substituted N-benzoyl intermediate XV, shown in Scheme VIII below.

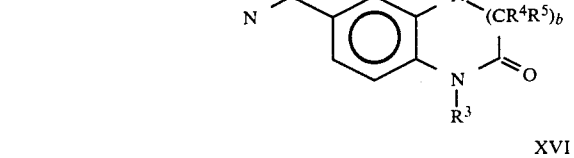

Treatment of intermediate XV with thiourea followed by acid hydrolysis removes the nitrogen protecting group and produces XVI.

The halo keto-intermediate XV may be prepared from the commercially available 1,2-dinitro-benzene as shown in Scheme IX, below.

Scheme IX

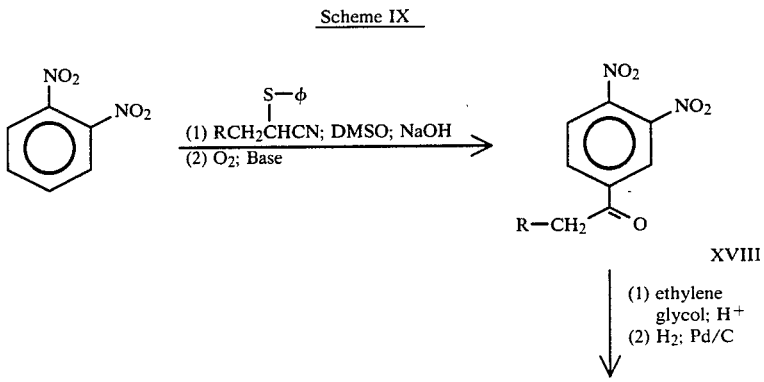

Scheme IX

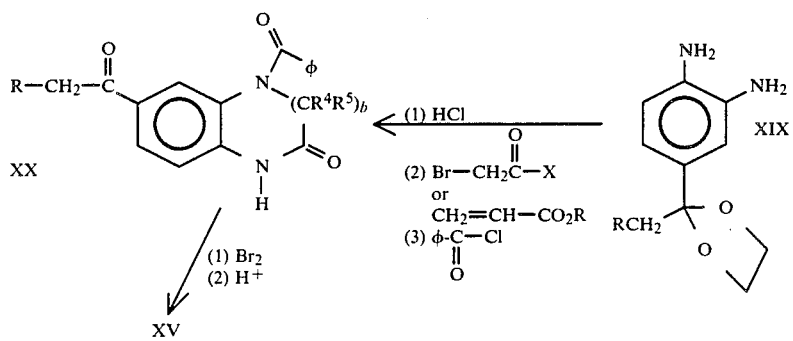

The dinitro-phenyl ketone intermediate XVIII may be prepared by the nucleophilic aromatic substitution of a phenyl hydrogen by treating the dinitro-phenyl group with sodium hydroxide and an alpha-phenylmercaptyl alkyl nitrile in DMSO, followed by oxidative decyanation with molecular oxygen and base. The ketone functionality is protected by cyclization to the ketal, and the nitro groups are reduced under standard catalytic hydrogenation conditions (5% Pd/C) to the diamine compound XIX. The diamine is treated with aqueous acid to deprotect the ketone followed by reaction with an alpha, beta unsaturated carboxylic acid (or alkyl ester) or halo acetic acid (or alkyl ester), such as bromo acetic acid followed by acid or base treatment to the bicyclic intermediate. See, G. A. Archer & L. H. Sternbach, Chem. Rev. 68, 747–784, 1968; and G. B. Bachman & L. V. Heisey, J. Am. Chem. Soc. 71, 1985, 1949. Treatment of the bicyclic amine with benzoyl chloride in the presence of a non-nucleophilic base such as triethylamine results in the N-benzoylated intermediate XX.

The N-protected bicyclic ketone intermediate may be brominated selectively at the position alpha to the ketone carbonyl to form bromo intermediate XV. Reaction conditions include either bromine in an aprotic polar solvent or a two-step procedure comprising treating the ketone with trimethylsilyl chloride in the presence of triethylamine in DMF followed by quenching the reaction product with one equivalent of bromine.

The N-benzoyl intermediate XX may also be prepared starting from para-amino alkyl phenyl ketone as shown in Scheme X below.

Scheme X

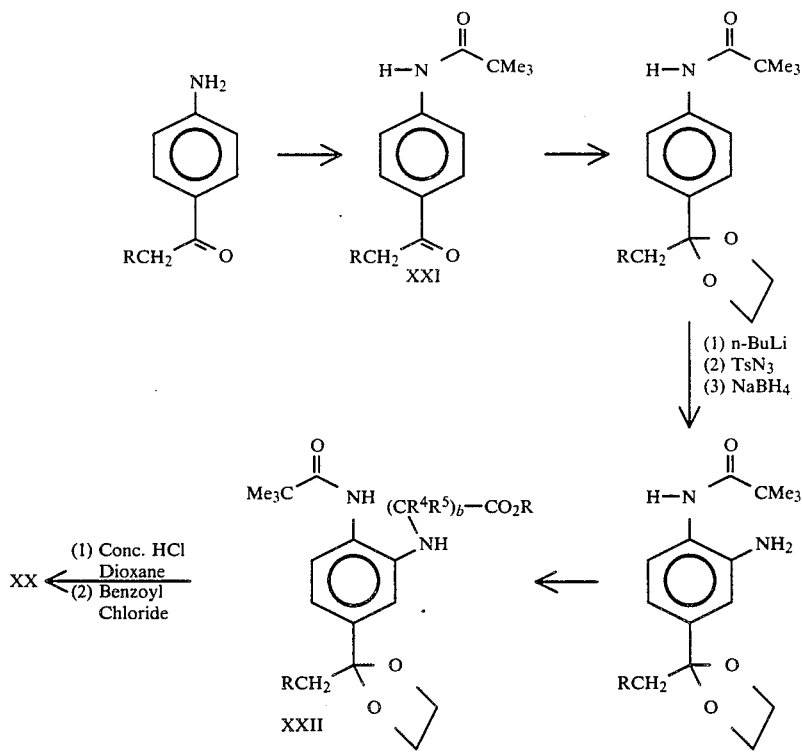

Protection of the para-amino group with trialkylacetyl chloride followed by conversion of the ketone carbonyl to the ethylene glycol ketal results in the intermediate XXI. Selective metallation of the ortho phenyl position with n-butyl lithium followed by treatment with tosyl azide and sodium borohydride results in the ortho-amine intermediate. Treatment of the amine with an appropriately substituted alkyl ester of an α-haloacetic acid or a 1,2-unsaturated acrylic acid ester produces the intermediate XXII, which, upon treatment with concentrated HCl in refluxing dioxane, cyclizes to the bicyclic compound and loses the ketal group. Benzoyl chloride may then be used to protect the amine in the subsequent reaction steps.

Examples of the preparation of compounds within the scope of the present invention are presented below.

EXAMPLE 1

THE PREPARATION OF 6-(2'-AMINOTHIAZOLE-4'-YL)-3,4-DIHYDRO-2(1H)-QUINAZOLINONE

Step 1: 6-(Bromoacetyl)-3,4-dihydro-2(1H)-quinazolinone

Bromoacetyl chloride (6.2 g) is added dropwise to a stirring mixture of 3,4-dihydro-2(1H)-quinazolinone (2.6 g) and anhydrous aluminum chloride (6.3 g) in carbon disulfide (60 ml). The reaction mixture is stirred under reflux for 4.5 hours, the carbon disulfide decanted, and the residue treated with HCl (6N). The resulting solid is poured into ice water, filtered, the filtered solid washed with water and dried in vacuo, affording the desired product, which is used in the next step without further purification.

Step 2: 6-(2'-Aminothiazole-4'-yl)-3,4-dihydro-2(1H)-quinazolinone

A mixture of the bromoacetyl compound obtained in Step 1. above (3 g) and thiourea (0.9 g) in absolute ethanol (40 ml) is refluxed for three hours. The reaction mixture is cooled to RT, filtered, and the filtered solid washed, dried and recrystallized from hot water. The recrystallized solid is stirred with sat'd. aqueous bicarbonate, filtered, dried, suspended in absolute ethanol and methanesulfonic acid added. The solid is filtered and dried in vacuo, affording the desired product as the methanesulfonate hemihydrate, M.P. 212° C. (dec).

EXAMPLE 2

THE PREPARATION OF 6-(2'-AMINO-5'-METHYLTHIAZOLE-4'-YL)-3,4-DIHYDRO-2(1H)-QUINAZOLINONE

Step 1: 6-(2-Bromopropionyl)-3,4-dihydro-2(1H)-quinazolinone

2-Bromopropionyl bromide (10.6 g) is added dropwise to a stirring mixture of 3,4-dihydro-2(1H)-quinazolinone (3.2 g) and anhydrous aluminum chloride (7.9 g) in carbon disulfide (60 ml). The reaction mixture is refluxed for four hours, the carbon disulfide decanted and the residue treated with aqueous hydrochloric acid (6N). The acidic residue is poured into ice water, and the precipitate filtered, washed with water and dried, affording the desired product as a solid, which is used in the next step without further purification.

Step 2: 6-(2'-Amino-5'-methylthiazole-4'-yl)-3,4-dihydro-2(1H)quinazolinone

A mixture of the bromopropionyl quinazolinone obtained in Step 1. (5 g) and thiourea (1.5 g) in absolute ethanol (50 ml) is refluxed for 4.5 hours. The reaction mixture is cooled to RT, filtered, and the precipitate suspended in sat'd aqueous sodium bicarbonate. The suspension is filtered, and the filtered solid suspended in absolute ethanol, and methanesulfonic acid (1.25 ml) added. The precipitate is filtered and dried, affording the desired product as an off-white methanesulfonate, M.P. 255° C. (dec).

EXAMPLE 3

THE PREPARATION OF 6-(2'-AMINOTHIAZOLE-4'YL)-3,4-DIHYDRO-3-METHYL-2(1H)-QUINAZOLINONE

Step 1: 6-(Bromoacetyl)-3,4-dihydro-3-methyl-2(1H)-quinazolinone

Bromoacetyl chloride (4.8 g) is added dropwise to a stirring solution of 3,4-dihydro-3-methyl-2(1H)-quinazolinone (2.5 g) and anhydrous aluminum chloride (4.9 g) in carbon disulfide (50 ml) under nitrogen. The reaction mixture is refluxed for five hours, cooled to RT and the carbon disulfide decanted. The residue is treated with hydrochloric acid (6N) and the acidic residue poured into ice water, stirred and filtered. The filtered solid is washed with water and dried in vacuo, affording the desired product, which is used in the next step without further purification, M.P. 190°–200° C. (dec).

Step 2: 6-(2'-aminothiazole-4'-yl)-3,4-dihydro-3-methyl-2(1H)-quinazolinone

A mixture of the bromoacetyl quinazolinone obtained in Step 1. (3 g) and thiourea (0.8 g) in absolute ethanol (35 ml) is refluxed for 3.5 hours. The reaction mixture is cooled to RT, filtered, and the filtered solid washed with ethanol and dried. The dried solid is suspended in sat'd. aqueous sodium bicarbonate solution, stirred, filtered, and the filtered solid dried and suspended in absolute ethanol. Methanesulfonic acid (1 ml) is added to the ethanolic suspension and the precipitate filtered, washed with absolute ethanol and dried in a vacuum desiccator, affording the desired product as the methanesulfonic salt ¼ hydrate, M.P. 265°–267° C. (dec).

EXAMPLE 4

THE PREPARATION OF 6-(2'-AMINO-5'-METHYLTHIAZOLE-4'-YL)-3,4-DIHYDRO-3-METHYL-2(1H)-QUINAZOLINONE

Step 1: 6-(2-Bromopropionyl)-3,4-dihydro-3-methyl-2(1H)-quinazolinone

2-Bromopropionyl bromide (6.7 g) is added dropwise to a stirring mixture of 3,4-dihydro-3-methyl-2(1H)-quinazolinone (2.5 g) and anhydrous aluminum chloride (4.9 g) in carbon disulfide (50 ml) under nitrogen. The reaction mixture is refluxed for five hours, cooled to RT, the carbon disulfide decanted, and the residue treated with hydrochloric acid (6N). The treated residue is poured into ice water, and the resulting suspension is stirred, filtered, the filtered solid washed with water, and dried in vacuo, affording the desired product, which is used in the next step without further purification, M.P. 150°–165° C. (dec).

Step 2: 6-(2'-Amino-5'-methylthiazole-4'-yl)-3,4-dihydro-3-methyl-2(1H)-quinazolinone A mixture of the bromopropionyl compound obtained in Step 1. (3 g) and thiourea (0.8 g) in absolute ethanol (35 ml) is refluxed for 6.5 hours. The reaction mixture is cooled to RT, filtered, and the solid washed in absolute ethanol and dried in vacuo. The dried solid is stirred in st'd aqueous sodium bicarbonate, filtered, and the filtered solid dried and suspended in absolute ethanol. Methanesulfonic acid (1 ml) is added to the ethanolic suspension, and the precipitate filtered, washed with absolute ethanol and dried in vacuo, affording the desired product as the methane sulfonate hemihydrate, M.P. 215°–235° C. (dec).

EXAMPLE 5

THE PREPARATION OF 6-(2'-AMINOTHIAZOLE-4'-YL)-3,4-DIHYDRO-4-METHYL-2(1H)-QUINAZOLINONE

Step 1: 6-(2-Bromoacetyl)-3,4-dihydro-4-methyl-2(1H)-quinazolinone

2-Bromoacetyl chloride (9.7 g) is added dropwise to a stirred mixture of 3,4-dihydro-4-methyl-2(1H)-quinazolinone (5 g), anhydrous aluminum chloride (10.3 g) and carbon disulfide (100 ml) under nitrogen. The reaction mixture is refluxed for about 18 hours, the carbon disulfide decanted, and the residue treated with hydrochloric acid (6N) and ethyl acetate. The layers are separated, and the aqueous layer extracted with ethyl acetate and the combined ethyl acetate extracts washed with sat'd. aqueous sodium bicarbonate and water and dried. The dried organic extract is filtered and the filtrate evaporated, affording the desired product as a solid, which is used without further purification, M.P. 188°–190° C.

Step 2: 6-(2'-Amino-thiazole-4'-yl)-3,4-dihydro-4-methyl-2(1H)-quinazolinone

The mixture of the bromoacetyl compound obtained in Step 1. (4 g) and thiourea (1.1 g) in absolute ethanol (30 ml) is refluxed overnight. The reaction mixture is cooled to RT, filtered, and the filtered solid washed with isopropyl alcohol and dried. The dried solid is suspended in sat'd aqueous sodium bicarbonate, filtered, and the filtered solid washed with water and dried. The solid is suspended in absolute ethanol, through which is bubbled hydrogen chloride gas. The resulting precipitate is filtered, washed with isopropyl alcohol and dried in vacuo, affording the desired product as the hydrochloride-1.25 hydrate, M.P. 245°–255° C.

EXAMPLE 6

THE PREPARATION OF 6-(2'-AMINO-5'-METHYLTHIAZOLE-4'-YL)-3,4-DIHYDRO-4-METHYL-2(1H)-QUINAZOLINONE

Step 1: 6-(2-Bromopropionyl)-3,4-dihydro-4-methyl-2(1H)-quinazolinone

2-Bromopropionyl bromide (16 g) is added dropwise to a mixture of 3,4-dihydro-4-methyl-2(1H)-quinazolinone (6.1 g) and anhydrous aluminum chloride (12.5 g) in carbon disulfide (110 ml). The reaction mixture is refluxed overnight under nitrogen, the carbon disulfide is decanted and the residue treated with hydrochloric acid (6N). The acidic residue is treated with ethyl acetate and the layers separated. The aqueous layer is extracted with ethyl acetate and the combined organic extracts washed with sat'd. aqueous sodium bicarbonate and water and dried. The organic layer is filtered and the filtrate stripped in vacuo, affording an oil which crystallizes in vacuo, M.P. 153°–156° C.

Step 2: 6-(2'-Amino-5'-methylthiazole-4'-yl)-3,4-dihydro-4-methyl-2(1H)-quinazolinone The mixture of the bromopropionyl quinzolinone compound obtained in Step 1. (8 g) and thiourea (2 g) in absolute ethanol (40 ml) is refluxed overnight. The reaction mixture is cooled to RT, filtered, and the filtered solid washed with isopropanol and dried. The dried solid is suspended in sat'd aqueous sodium bicarbonate, filtered, and the filtered solid suspended in absolute ethanol and methanesulfonic acid added. The precipitate is filtered, washed with isopropanol and dried in vacuo, affording the desired product as the methanesulfonate ¼ hydrate, M.P. 278°–280° C.

Tables I through VII list compounds which are also within the scope of the present invention.

TABLE I

| R | $R^1$ | $R^2$ | $R^3$ | $R^6$ |
|---|---|---|---|---|
| H | H | H | H | H |
| $CH_3$ | H | H | H | H |
| H | H | H | $CH_3$ | H |
| $CH_3$ | $CH_3$ | H | H | H |
| H | H | $CH_3$ | $CH_3$ | H |
| $CH_3$ | H | H | H | $CH_3$ |
| Et | H | H | H | H |
| H | $CH_3$ | H | H | H |
| H | $CH_3$ | H | $CH_3$ | H |

TABLE II

| R | $R^1$ | $R^2$ | $R^3$ | $R^4$ | $R^5$ | $R^6$ |
|---|---|---|---|---|---|---|
| H | H | H | H | H | H | H |
| $CH_3$ | H | H | H | H | H | H |
| H | H | $CH_3$ | H | H | H | H |
| H | H | H | $CH_3$ | H | H | H |
| H | H | H | H | $CH_3$ | H | H |
| H | H | H | H | H | H | $CH_3$ |
| $CH_3$ | H | $CH_3$ | H | H | H | H |
| $CH_3$ | H | H | $CH_3$ | H | H | H |
| H | H | $CH_3$ | $CH_3$ | H | H | H |
| $CH_3$ | H | H | H | H | H | $CH_3$ |
| H | H | H | H | $CH_3$ | $CH_3$ | H |
| H | H | H | H | $CH_3$ | H | $CH_3$ |
| $CH_3$ | H | H | H | $CH_3$ | H | H |
| $CH_3$ | H | H | H | $CH_3$ | H | $CH_3$ |
| $CH_3$ | H | $CH_3$ | H | H | H | $CH_3$ |
| $CH_3$ | H | $CH_3$ | $CH_3$ | H | H | H |
| H | H | $CH_3$ | H | $CH_3$ | $CH_3$ | H |
| $CH_3$ | H | H | H | H | H | H |
| H | $CH_3$ | $CH_3$ | H | H | H | H |
| $CH_3$ | H | H | H | H | H | $CH_3$ |
| Et | H | H | H | H | H | H |
| n-$C_3H_7$ | H | H | H | H | H | H |
| H | H | n-$C_3H_7$ | H | H | H | H |
| H | H | H | H | Et | H | H |
| H | H | H | H | H | H | $\phi CH_2-$ |
| H | H | H | H | H | H | $\phi CH_2CH_2-$ |
| H | H | H | H | $\phi CH_2-$ | H | H |
| $\phi CH_2$ | H | H | H | H | H | H |
| $CH_3$ | H | H | H | H | H | $\phi CH_2-$ |
| H | H | H | H | H | H | H |
| H | H | $CH_3$ | H | H | H | H |
| H | H | H | H | H | H | $CH_3$ |
| H | H | H | H | $CH_3$ | H | H |
| H | H | H | H | $CH_3$ | H | $CH_3$ |
| $CH_3$ | H | H | H | H | H | H |
| H | $CH_3$ | $CH_3$ | H | H | H | H |
| H | H | H | H | $-CH_2CH_2CH_2-$ | | H |
| H | H | H | H | $-CH_2CH_2CH_2CH_2-$ | | H |
| $CH_3$ | H | H | H | $-CH_2CH_2CH_2CH_2-$ | | H |

TABLE III

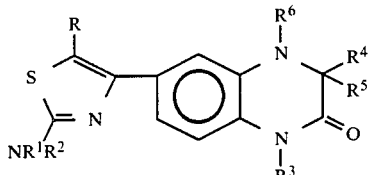

| R | R¹ | R² | R³ | R⁴ | R⁵ | R⁶ |
|---|---|---|---|---|---|---|
| H | H | H | H | H | H | H |
| CH₃ | H | H | H | H | H | H |
| H | H | H | H | CH₃ | H | H |
| H | H | H | H | CH₃ | CH₃ | H |
| CH₃ | CH₃ | H | H | H | H | H |
| H | H | CH₃ | H | H | H | H |
| H | H | H | CH₃ | H | H | H |
| H | H | H | H | CH₂φ | H | H |
| H | H | H | H | H | H | H |
| H | H | H | H | CH₃ | CH₃ | H |
| H | H | H | H | H | H | CH₃ |

TABLE IV

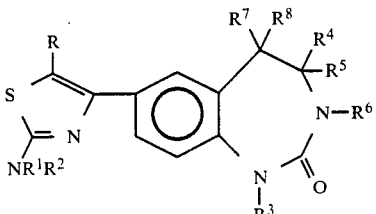

| R | R¹ | R² | R³ | R⁴ | R⁵ | R⁶ | R⁷ | R⁸ |
|---|---|---|---|---|---|---|---|---|
| H | H | H | H | H | H | H | H | H |
| H | H | H | H | CH₃ | H | H | H | H |
| H | H | H | H | H | H | H | CH₃ | H |
| CH₃ | H | H | H | H | H | H | H | H |
| H | H | H | H | H | H | CH₃ | H | H |
| H | H | H | H | H | H | Et | H | H |
| H | H | H | H | H | H | φCH₂ | H | H |
| H | H | H | H | CH₃ | CH₃ | H | H | H |
| H | H | H | H | —CH₂CH₂CH₂CH₂— | H | H | H |
| H | CH₃ | H | H | H | H | H | H | H |
| H | CH₃ | H | H | H | CH₃ | H | H | H |

TABLE V

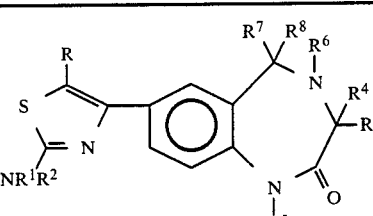

| R | R¹ | R² | R³ | R⁴ | R⁵ | R⁶ | R⁷ | R⁸ |
|---|---|---|---|---|---|---|---|---|
| H | H | H | H | H | H | H | H | H |
| H | H | CH₃ | H | H | H | H | H | H |
| H | H | H | H | H | H | CH₃ | H | H |
| CH₃ | CH₃ | H | H | H | H | H | H | H |

TABLE VI

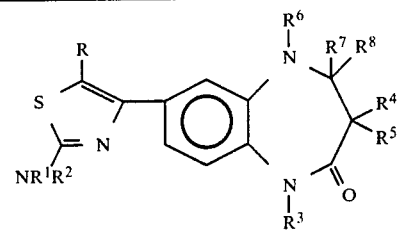

| R | R¹ | R² | R³ | R⁴ | R⁵ | R⁶ | R⁷ | R⁸ |
|---|---|---|---|---|---|---|---|---|
| H | H | H | H | H | H | H | H | H |
| H | H | CH₃ | H | H | H | H | H | H |
| H | H | H | H | H | H | CH₃ | H | H |
| H | H | H | H | CH₃ | H | H | H | H |
| H | H | H | H | CH₃ | H | CH₃ | H | H |
| CH₃ | CH₃ | H | H | H | H | H | H | H |

TABLE VII

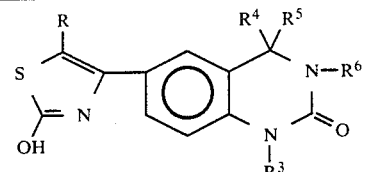

| R | R³ | R⁴ | R⁵ | R⁶ |
|---|---|---|---|---|
| H | H | H | H | H |
| CH₃ | H | H | H | H |
| H | H | H | H | H |
| H | CH₃ | H | H | H |
| H | H | CH₃ | H | H |
| H | H | H | H | CH₃ |
| CH₃ | H | H | H | H |
| CH₃ | CH₃ | H | H | H |
| H | CH₃ | H | H | H |
| CH₃ | H | H | H | CH₃ |
| H | H | CH₃ | CH₃ | H |
| H | H | CH₃ | H | CH₃ |
| CH₃ | H | CH₃ | H | H |
| CH₃ | H | CH₃ | H | CH₃ |
| CH₃ | H | H | H | CH₃ |
| CH₃ | H | CH₃ | H | H |
| H | H | CH₃ | CH₃ | H |
| CH₃ | H | H | H | H |
| H | H | H | H | H |
| CH₃ | H | H | H | CH₃ |
| Et | H | H | H | H |
| n-C₃H₇ | H | H | H | H |
| H | H | H | H | H |
| H | H | Et | H | φCH₂— |
| H | H | H | H | φCH₂CH₂— |
| H | H | φCH₂— | H | H |
| φCH₂ | H | H | H | φCH₂— |
| CH₃ | H | H | H | H |
| H | H | H | H | H |
| H | H | H | H | CH₃ |
| H | H | CH₃ | H | H |
| H | H | CH₃ | H | CH₃ |
| CH₃ | H | H | H | H |
| H | H | H | H | H |
| H | H | —CH₂CH₂CH₂— | H |
| H | H | —CH₂CH₂CH₂— | H |
| CH₃ | H | —CH₂CH₂CH₂CH₂— | H |

The compounds of Formula I possess positive inotropic activity and are useful as cardiotonic agents in the treatment of humans and other animals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

Anesthetized Dog Procedure

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

The results of the anesthetized dog test show that the compounds of this invention exhibit positive inotropic activity and show dose related increases in contractile force with relatively small increases in heart rate.

Two additional test procedures which have been found to be an efficient means for ascertaining the inotropic activity of the compounds of this invention are described below.

Conscious Instrumented Dog

Female mongrel dogs (18.0–18.5 kg) are anesthetized with sodium pentobarbital (35 mg/kg i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to her environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular and diastolic pressure, left ventricular $dP/dt_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

Guinea Pig Atria Inotropic Screening at Low Calcium Concentrations

Guinea pigs are stunned by a sudden blow to the head; their chests are opened and hearts excised and placed in Kreb's medium (concentrations, mM: NaCl, 118.39; KCl, 4.70; $MgSO_4$, 1.18; $KH_2PO_4$, 1.18; $NaHCO_3$, 25.00; glucose, 11.66; and $CaCl_2$, 1.25) gassed with a mixture of 95% $O_2$-5% $CO_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 20-gauge silver wire wound into a tight coil approximately 12–14 mm in diameter. Electrodes are connected to a Grass stimulator via a Grass constant current unit. Tissues are driven at 90 pulses per minute with a 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions are calculated via the method of Finney (1971) and compared using Student's t-test.

The compounds of this invention can be normally administered orally or parenterally, in the treatment of cardiac disorders such as heart failure in humans or other mammals.

The compounds of this invention may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, and particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the method of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

We claim:
1. A compound of the formula

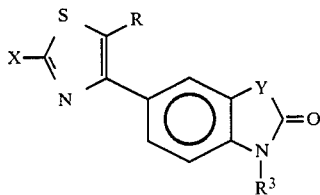

wherein:
X is NR$^1$R$^2$ or OH;
Y is

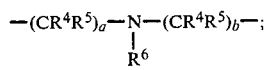

a and b are 0, 1 or 2, provided that a+b is not greater than 2;
R, R$^1$, R$^2$, R$^3$, R$^4$, R$^5$ and R$^6$ are each independently H, lower alkyl or lower alkyl substituted by phenyl or phenyl substituted by one or more of lower alkyl, lower alkoxy, amino, lower alkyl amino, lower alkyl mercapto, hydroxy, hydroxy lower alkyl, acetoxy, benzyloxy, phenoxy, lower alkyl sulfinyl or lower alkyl sulfonyl;
R$^4$ groups on vicinal carbon atoms may together form a carbon-carbon double bond; and
geminal R$^4$ and R$^5$ groups may together form a spiro substituent, —(CH$_2$)$_d$—, where d is 2 to 5; or a pharmaceutically acceptable salt thereof.

2. A compound according to claim 1 wherein:
Y is

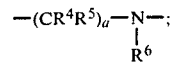

and
a is 1 or 2.
3. A compound according to claim 1 wherein:
Y is

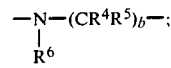

and
b is 1 or 2.
4. A compound according to claim 2 wherein:
a is 1.
5. A compound according to claim 1 wherein:
a is 1 and b is 1.
6. A compound according to claim 1 wherein:
a is 0 and b is 0.
7. A compound according to claim 4 wherein:
x is OH.
8. A compound according to claim 4 wherein:
R$^1$ and R$^2$ are hydrogen.
9. A compound according to claim 7 or 8 wherein:
R$^3$, R$^4$, R$^5$ and R$^6$ are hydrogen or lower alkyl.
10. A compound according to claim 7 or 8 wherein:
R$^3$ or R$^4$ or R$^6$ is lower alkyl.
11. A compound according to claim 2 wherein:
a is 2.
12. A compound according to claim 10 wherein:
lower alkyl is methyl.
13. A compound according to claim 1 which is 6-(2'-aminothiazole-4'-yl)-3,4-dihydro-2(1H)-quinazolinone, or a pharmaceutically acceptable salt thereof.
14. A compound according to claim 1 which is 6-(2'-amino-5'-methylthiazole-4'-yl)-3,4-dihydro-2(1H)-quinazolinone, or a pharmaceutically acceptable salt thereof.
15. A compound according to claim 1 which is 6-(2'-aminothiazole-4'-yl)-3,4-dihydro-3-methyl-2(1H)-quinazolinone, or a pharmaceutically acceptable salt thereof.
16. A compound according to claim 1 which is 6-(2'-amino-5'-methylthiazole-4'-yl)-3,4-dihydro-3-methyl-2(1H)-quinazolinone, or a pharmaceutically acceptable salt thereof.
17. A compound according to claim 1 which is 6-(2'-aminothiazole-4'-yl)-3,4-dihydro-4-methyl-2(1H)-quinazolinone, or a pharmaceutically acceptable salt thereof.
18. A compound according to claim 1 which is 6-(2'-amino-5'-methylthiazole-4'-yl)-3,4-dihydro-4-methyl-2(1H)-quinazolinone, or a pharmaceutically acceptable salt thereof.
19. A compound according to claim 1 which is 5-(2'-hydroxythiazole-4'-yl)-3,4-dihydro-2(1H)-quinazolinone, or a pharmaceutically acceptable salt thereof.
20. A method for increasing cardiotonic contractility in a patient requiring such treatment which comprises administering to such patient an effective amount of compound according to claim 1.
21. A pharmaceutical composition for increasing cardiotonic contractility in a patient requiring such treatment comprising a compound according to claim 1.

* * * * *

UNITED STATES PATENT AND TRADEMARK OFFICE
CERTIFICATE OF CORRECTION

PATENT NO. : 4,666,913

DATED : May 19, 1987

INVENTOR(S) : Donald E. Kuhla et al

It is certified that error appears in the above-identified patent and that said Letters Patent is hereby corrected as shown below:

Title page under UNITED STATES PATENT [19]    "Kubla et al." should read --Kuhla et al.--.

Title page at [75]    "Donald E. Kubla" should read --Donald E. Kuhla--.

Signed and Sealed this

Third Day of November, 1987

Attest:

DONALD J. QUIGG

Attesting Officer    Commissioner of Patents and Trademarks